United States Patent [19]

Christians

[11] Patent Number: 5,030,268
[45] Date of Patent: Jul. 9, 1991

[54] PREEMERGENCE WEED CONTROL USING CORN GLUTEN MEAL

[75] Inventor: Nick E. Christians, Ames, Iowa

[73] Assignee: Iowa State University Research Foundation, Inc., Ames, Iowa

[21] Appl. No.: 465,475

[22] Filed: Jan. 16, 1990

[51] Int. Cl.$^5$ ..................... A01N 65/00; A01N 31/08
[52] U.S. Cl. ........................................................ 71/79
[58] Field of Search .................................... 71/122, 79

[56] References Cited

U.S. PATENT DOCUMENTS

| | | | |
|---|---|---|---|
| 3,179,653 | 4/1965 | Sherwood | 260/210 |
| 3,360,356 | 12/1967 | Vartiak | 71/122 |
| 3,556,767 | 1/1971 | Mecklenborg | 71/122 |
| 4,164,405 | 8/1979 | Pinckard | 71/79 |
| 4,229,442 | 10/1980 | Pinckard | 424/195 |
| 4,579,579 | 4/1986 | Kerr | 71/23 |
| 4,755,207 | 7/1988 | Bannon | 71/79 |

OTHER PUBLICATIONS

Goetze, N. R. et al., "Nirtogen Fairway Fertilization Research", *Midwest Turf*, No. 15, Purdue University, Feb. 1957.

*Primary Examiner*—Glennon H. Hollrah
*Assistant Examiner*—S. Mark Clark
*Attorney, Agent, or Firm*—Zarley, McKee, Thomte, Voorhees, & Sease

[57] ABSTRACT

Corn gluten meal is used as a natural preemergence herbicide.

4 Claims, No Drawings

PREEMERGENCE WEED CONTROL USING CORN GLUTEN MEAL

FIELD OF THE INVENTION

This invention relates to a natural herbicide which may be applied to soil plots to achieve preemergence weed control as a substitute for chemical herbicides or as a supplement to chemical herbicides to reduce their concentration in the environment.

BACKGROUND OF THE INVENTION

The use of herbicides to control undesirable weeds in a selective fashion is commonplace. Chemical herbicides are a large business, and involve millions of pounds of herbicide applied directly to the soil on an annual basis. An effective herbicide must not only control undesirable plants, dubbed weeds, but must also control them in a selective manner so that desired plants will grow. Preemergence herbicides refer to those which must be applied before the weed emerges from the soil.

In recent times, especially since environmental awareness has increased, many herbicides, including many preemergence herbicides have come under disfavor as chemical pollutants. This is especially true in areas of the country where these preemergence herbicides are applied in large quantities. It has now come to be recognized by many groups and associations, including the Environmental Protection Agency, that these preemergence herbicides may have an undesirable polluting effect, not only on the soil, but on the level of contamination in ground water, etc.

There is, therefore, a real and continuing need to develop natural herbicides. As used herein, natural herbicides refers to herbicides that come naturally from available growing, safe substances. One example of natural treatments for soil includes biological controls such as the addition of specific bacteria to accomplish a desired result. Another more common example of natural product application to soils would be manure as a fertilizer.

Natural herbicides would have a distinct advantage in that they would be safe materials, and materials which would not cause any concern for possible contamination of ground water from runoff or soil movement.

Accordingly, it is a primary objective of the present invention to provide a natural preemergence herbicide useful in controlling weeds such as crabgrass, smart weed, barnyard grass, etc.

Another objective of the present invention is to provide a natural preemergence herbicide from corn gluten meal extracted from corn meal.

Another objective of the present invention is to provide a natural corn gluten meal preemergence herbicide which can be used as a substitute for chemical herbicides or as a supplement to chemical herbicides to reduce their concentration in the environment.

A still further objective of the present invention is to provide a method and means of preemergence control of annual grass weeds.

The method and manner of accomplishing each of the above objectives, as well as others, will become apparent from the description of the invention which follows hereinafter.

SUMMARY OF THE INVENTION

In accordance with this invention, preemergence weed control is accomplished by applying to a soil plot, prior to weed emergence, a herbicidally effective amount of corn gluten meal. Corn gluten meal, when applied in this pre-emergence manner functions to selectively inhibit annual grassy weeds.

DETAILED DESCRIPTION OF THE INVENTION

As earlier stated, this invention involves preemergence weed control. Preemergence, as those skilled in the art know, refers to weed control substances which must be applied before emergence of the annual grassy weeds, usually in the Spring. There are of course many commercially available preemergence chemical controls. In accordance with this invention, a preemergence weed control which is natural and not subject to the ordinary environmental risks is provided. The natural weed control substance of the present invention is corn gluten meal. Corn gluten meal is a fraction extracted from corn meal. When the corn gluten meal is applied to a soil plot prior to weed emergence in a small but herbicidally effective amount, it will selectively inhibit undesirable plants such as annual grassy weeds. Plants known to be effectively inhibited in a preemergence manner by the application of corn gluten meal include, but are not necessarily limited to crabgrass, creeping bentgrass, smart weed, barnyard grass, Bermuda grass and tall fescue. The amount of corn gluten meal which can be applied can vary over a wide range, but is generally within the range of a concentration from about 5 lbs./1000 sq. ft. to about 40 lbs./1000 sq. ft., preferably from about 10 lbs./1000 sq. ft. to about 30 lbs./1000 sq. ft. and optimally, at about 20 lbs./1000 sq. ft.

The manner of addition of the corn gluten meal is the same as any other conventional preemergence herbicide and it can be applied by the use of a conventional lawn fertilizer spreader. It can be in the form of a dust, powder, pellets, etc.

Corn gluten meal is a commercially available material extracted from corn meal. It is commercially available from many sources such as Grain Processing Corporation of Muscatine, Iowa, 52761. Generally, as those skilled in the art know, corn gluten meal is made by drying the liquid gluten stream separated from corn during corn wet milling processing. While its composition can vary, it commonly contains about 60% protein and is rich in xanthophills. It is a mixture of protein, lipid, carbohydrate and ash material. While corn gluten meal is known, and has been commercially available, in the past its primary usage has been as a feed substance for use with broilers, etc.

It is important to note in accordance with the present invention that the material applied as a preemergence herbicide is corn gluten meal, not corn meal. Corn gluten meal, as earlier stated, differs considerably from corn meal in that it is extracted material made by drying the liquid gluten stream separated from corn during the corn wet milling processing. Thus, it represents a fortified material in comparison with corn meal. Corn meal itself has been tried as a preemergence herbicide for use in the present invention. Corn meal is somewhat effective, but corn gluten meal is much more effective.

It is not known precisely why corn gluten meal functions effectively as a natural preemergence herbicide.

While applicant does not wish to be bound by any theory, based upon investigations to date, it is believed that the corn gluten meal when applied to a soil plot, selectively stops root development of annual grassy weeds almost precisely at the time of germination. As a result, as soon as the plant begins to grow, it will undergo root stress and die. Thus, for some unknown reason, while the corn gluten meal does not prohibit germination, it nevertheless does not allow the root structure to develop sufficient that the weed can grow to a healthy plant. As a result, it dies from the lack of root growth. It is possible that some as of yet unidentified allelopathic compound is present in the corn gluten meal. If this be the case, it may also be possible to isolate the compound, and use it in a highly fortified manner. Alternatively, such a compound could be chemically synthesized and used or perhaps even produced biotechnically by bacterial substances.

As those skilled in the art know, preemergence herbicides are critical for application prior to weed emergence. The precise time of application will vary, depending upon the area of the country in which the natural herbicide of the present invention is applied and the weed species involved, but in general, for areas of the Midwest, application must be prior to May 1st of any growing season.

It is possible that other extracts of other grain meals may function in a similar manner, although others have not yet been tested. However, one such apparent material for possible use would be soybean meal.

The following examples are offered to illustrate the present invention, namely use of corn gluten meal as an effective natural preemergence herbicide.

EXAMPLE 1

To investigate the effect of cornmeal substances on seed germination, a greenhouse study was conducted. Samples of (1) industrial corn starch, (2) corn gluten meal, (3) dried corn germ, (4) corn seed fiber, and (5) cornmeal were applied to the surface of 16 square inch pots. The treatments included a control and each of the materials at 7 grams, 14 grams, and 28 grams per pot. The study was conducted with both plain and autoclaved samples of each corn component. All pots were seeded with creeping bentgrass.

The results of this study clearly showed that the component of the corn that contains the greatest concentration of the inhibitory substance is the corn gluten meal. All rates of this product completely inhibited the establishment of creeping bentgrass. Autoclaving had no effect, indicating that the inhibitory substance is heat stable. It was observed in the greenhouse trial that the effect of the corn materials is not to stop germination, but to stop root formation of the germinated seed. Germination occurs, but the seedling dies in a matter of days because of the lack of a root system.

EXAMPLE 2

In further greenhouse trials, it was observed that from 6 to 8 grams of corn gluten meal on a 16 square inch pot was sufficient to stop the establishment of creeping bentgrass. Corn gluten meal applied to established Kentucky bluegrass (*Poa pratensis*) had no detrimental effects at rates up to 20 grams per 16 square inch pot. In fact, the gluten improves plant growth, likely as a result of nitrogen release from protein. Trials with other plants species have shown that the inhibitory substance in the gluten meal is effective in preventing the establishment of crabgrass, smartweed, barnyardgrass, Kentucky bluegrass, perennial ryegrass, tall fescue, smooth bromegrass, and bermudagrass seed.

The information gathered from these example studies indicates that an allelopathic compound may exist in corn grain that has the ability to inhibit the establishment of a variety of plant species by stopping root formation during germination. This compound also seems safe for use on plants that have already been established.

EXAMPLE 3

In the following example, corn gluten meal was compared with Milorganite, a natural and long commercially available nitrogen source. They were compared in a crabgrass germination study.

In particular, crabgrass was seeded at a rate of 0.20 grams in 4"×4" pots and in a preemergence manner, certain levels of addition, namely 0 for a control, 2 grams, 4 grams, 6 grams, 8 grams, 10 grams and 12 grams of both corn gluten meal and Milorganite were added to the surface of the crabgrass seeded pots. The pots were grown and watered and the number of crabgrass plants were periodically observed. The following table illustrates the number of plants observed and the date and time of observance.

TABLE I

CRABGRASS CONTROL IN KENTUCKY BLUEGRASS TURF TREATED WITH CORN GLUTEN MEAL AND MILORGANITE

|  | CONTROL | 0.5 LBS N | 1.0 LBS N | 2.0 LBS N | 4.0 LBS N |
| --- | --- | --- | --- | --- | --- |
| CORN GLUTEN MEAL | 81 | 33 | 36 | 32 | 13 |
| MILORGANITE | 81 | 75 | 56 | 53 | 24 |

It can be seen from the above Table that corn gluten meal effectively functions to selectively inhibit crabgrass germination whereas a common natural nitrogen source, long commercially available Milorganite, does not act to the same extent.

What is claimed is:

1. A method for selectively inhibiting growth of undesirable annual and certain perennial grassy plants in an area containing an established plot of desirable grassy plants, said method comprising:
applying prior to emergence of undesirable grassy plants to said area at a concentration of application which inhibits growth of undesirable plants, corn gluten meal.

2. The method of claim 1 wherein the corn gluten meal is applied at concentrations of from about 5 lbs./1000 sq. ft. to about 40 lbs./1000 sq. ft.

3. The method of claim 2 wherein the corn gluten meal is applied at a concentration of about 20 lbs./1000 sq. ft.

4. The method of any one of claims 1, 2, or 3, wherein the desirable grassy plants are bluegrass turf.

* * * * *